US00RE51065E

(19) United States
(12) Reissued Patent
Stewart et al.

(10) Patent Number: US RE51,065 E
(45) Date of Reissued Patent: Oct. 13, 2026

(54) HOUSING FOR A MEDICAL INJECTOR

(71) Applicant: SHL MEDICAL AG, Zug (CH)

(72) Inventors: Justin Stewart, Deerfield Beach, FL (US); Jochen Ratjen, Nacka Strand (SE)

(73) Assignee: SHL Medical AG, Zug (CH)

(21) Appl. No.: 29/971,162

(22) Filed: Nov. 1, 2024

Related U.S. Patent Documents

Reissue of:
(64) Patent No.: Des. 1,031,023
Issued: Jun. 11, 2024
Appl. No.: 29/725,394
Filed: Feb. 25, 2020

U.S. Applications:
(62) Division of application No. 29/702,935, filed on Aug. 22, 2019, now Pat. No. Des. 884,161, which is a (Continued)

(51) LOC (15) Cl. ..... 24-02
(52) U.S. Cl.
USPC ..... D24/112
(58) Field of Classification Search
USPC ..... D24/112–114, 133, 186, 127–131, 231, D24/108

(Continued)

(56) References Cited

U.S. PATENT DOCUMENTS

D461,813 S * 8/2002 Chang ..... D13/174
7,488,297 B2 2/2009 Flaherty ..... A61B 5/150236 600/580

(Continued)

OTHER PUBLICATIONS

Markus Hoerburger, "Launching in an autoinjector: What to expect with a self-injection device", CDMO Insights, [Post date: Feb. 29, 2024], [Site seen: Oct. 7, 2025], URL: https://www.vetter-pharma.com/en/cdmo-insights/autoinjector-launch/ (Year: 2024).*

(Continued)

*Primary Examiner* — Darlington Ly
(74) *Attorney, Agent, or Firm* — McDonnell Boehnen Hulbert & Berghoff LLP

(57) CLAIM

The ornamental design for housing for a medical injector, as shown and described.

DESCRIPTION

FIG. 1 is a *front, top* perspective view of [the] *a* housing for a medical injector [viewed from the front top] *showing our new design*;
FIG. 2 is a [top plan] *rear, bottom perspective* view thereof*;*
FIG. 3 is a [bottom] *top* plan view thereof;
FIG. 4 is a [right side elevation] *bottom plan* view thereof;
FIG. 5 is a left side elevation view thereof;
FIG. 6 is a [rear] *right side* elevation view thereof;
FIG. 7 is a [front] *rear* elevation view thereof; and,
FIG. 8 is [close-up of a partial portion of FIG. 2] *a front elevation view thereof.*
The broken line showing is for the purpose of illustrating portions of the article [and forms] *that form* no part of the claimed design. [The broken line which defines the bounds of the claimed invention forms no part of the claimed design.]

1 Claim, 5 Drawing Sheets

Matter enclosed in heavy brackets [ ] appears in the original patent but forms no part of this reissue; matter printed in italics indicates the additions made by reissue.

(NEW)

Related U.S. Application Data division of application No. 29/617,342, filed on Sep. 13, 2017, now Pat. No. Des. 868,961.

(58) Field of Classification Search

CPC ..... A61M 5/3156; A61M 5/31591; A61M 5/3155; A61M 5/3157; A61M 5/31501

See application file for complete search history.

(56) References Cited

U.S. PATENT DOCUMENTS

| | | | | | |
|---|---|---|---|---|---|
| D619,244 | S | | 7/2010 | Van der Stappen | D24/113 |
| D627,061 | S | | 11/2010 | Van der Stappen | D24/113 |
| D696,774 | S | | 12/2013 | Guarraia et al. | D24/113 |
| D708,317 | S | | 7/2014 | Schneider et al. | D24/112 |
| 8,821,451 | B2 | | 9/2014 | Daniel | A61M 5/31511 604/137 |
| D714,932 | S | | 10/2014 | Hall et al. | D24/112 |
| 9,033,932 | B2 | | 5/2015 | Holmqvist | A61M 5/2033 604/187 |
| D733,869 | S | | 7/2015 | Ratjen | D24/113 |
| D757,255 | S | | 5/2016 | Wohlfahrt et al. | D24/113 |
| D758,567 | S | | 6/2016 | Wohlfahrt et al. | D24/113 |
| D758,569 | S | | 6/2016 | Wohlfahrt et al. | D24/113 |
| D758,570 | S | | 6/2016 | Wohlfahrt et al. | D24/113 |
| D758,571 | S | | 6/2016 | Geert-Jensen et al. | D24/113 |
| D767,119 | S | | 9/2016 | Hauck et al. | D24/113 |
| D774,641 | S | | 12/2016 | Miggels et al. | D24/112 |
| D794,178 | S | | 8/2017 | Daniel et al. | |
| D810,281 | S | | 2/2018 | Holmqvist et al. | A61M 5/31 D24/112 |
| D810,282 | S | | 2/2018 | Ratjen | D24/114 |
| 9,943,649 | B2 | | 4/2018 | Shang et al. | A61M 5/3157 |
| 9,981,087 | B2 | | 5/2018 | Shang et al. | A61M 5/2033 |
| D819,804 | S | | 6/2018 | Knight et al. | D24/113 |
| D824,023 | S | | 7/2018 | Grimoldby | D24/113 |
| D830,538 | S | | 10/2018 | Guillermo et al. | D24/112 |
| D831,822 | S | | 10/2018 | Guillermo et al. | D24/112 |
| D851,754 | S | | 6/2019 | Boyaval et al. | D24/113 |
| D883,475 | S | * | 5/2020 | Boyaval | D24/117 |
| D892,312 | S | * | 8/2020 | Nicholas | D24/113 |
| D895,106 | S | * | 9/2020 | Patil | D24/113 |
| D940,306 | S | * | 1/2022 | Osypka | D24/127 |
| D940,307 | S | * | 1/2022 | Osypka | A61B 18/1492 D24/127 |
| D954,941 | S | * | 6/2022 | Yuan | D24/144 |
| D956,211 | S | * | 6/2022 | Bourelle | D24/113 |
| D1,015,529 | S | * | 2/2024 | Cannamela | D24/113 |
| D1,015,531 | S | * | 2/2024 | Cannamela | D24/113 |
| D1,078,994 | S | * | 6/2025 | Kvist | D24/113 |
| D1,083,087 | S | * | 7/2025 | Kaare Soelberg | D24/113 |
| D1,084,306 | S | * | 7/2025 | Kaare Soelberg | D24/113 |
| D1,095,819 | S | * | 9/2025 | Melander | D24/113 |
| D1,097,129 | S | * | 10/2025 | Davis | D24/113 |
| D1,097,137 | S | * | 10/2025 | Lavmand Muller | D24/113 |

OTHER PUBLICATIONS

Maggie®, SHL Medical, [Post date: Jan. 20, 2025], [Site seen: Oct. 7, 2025], URL: https://www.shl-medical.com/products/autoinjectors/maggie (Year: 2025).*

McGowan M, "30 Years in the Making—An Inside Perspective On the Emergence of Autoinjectors" On Drug Delivery, [Post date Feb. 2, 2019], [Site seen: Oct. 19, 2025], URL: https://www.ondr ugdelivery.com/30-years-in-the-making-an-inside-perspective-on-the-emergence-of-autoinj ectors / (Year: 2019).*

Author unknown, "Going big: How cartridges are making large-volume . . . ," Pharmaceutical Technology, [Post date: Apr. 17, 2023], [Site seen: Oct. 19, 2025], URL: https://www.pharmaceutical-technology.com/sponsored/going-big-how-cartridges-are-making-large-volume-high-dose-subcutaneous-autoinjectors-a-reality/ (Year: 2023).*

* cited by examiner

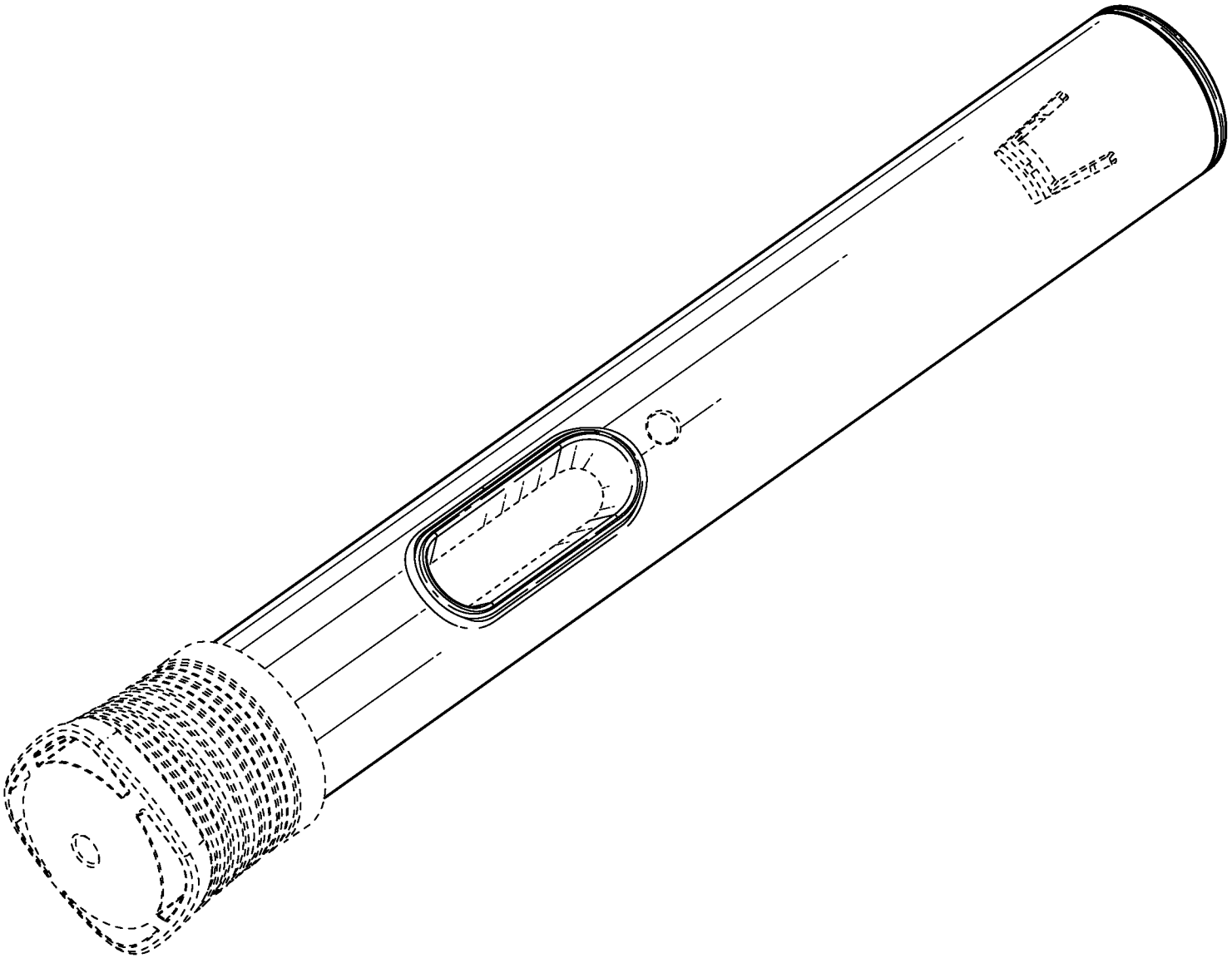
FIG. 1
(NEW)

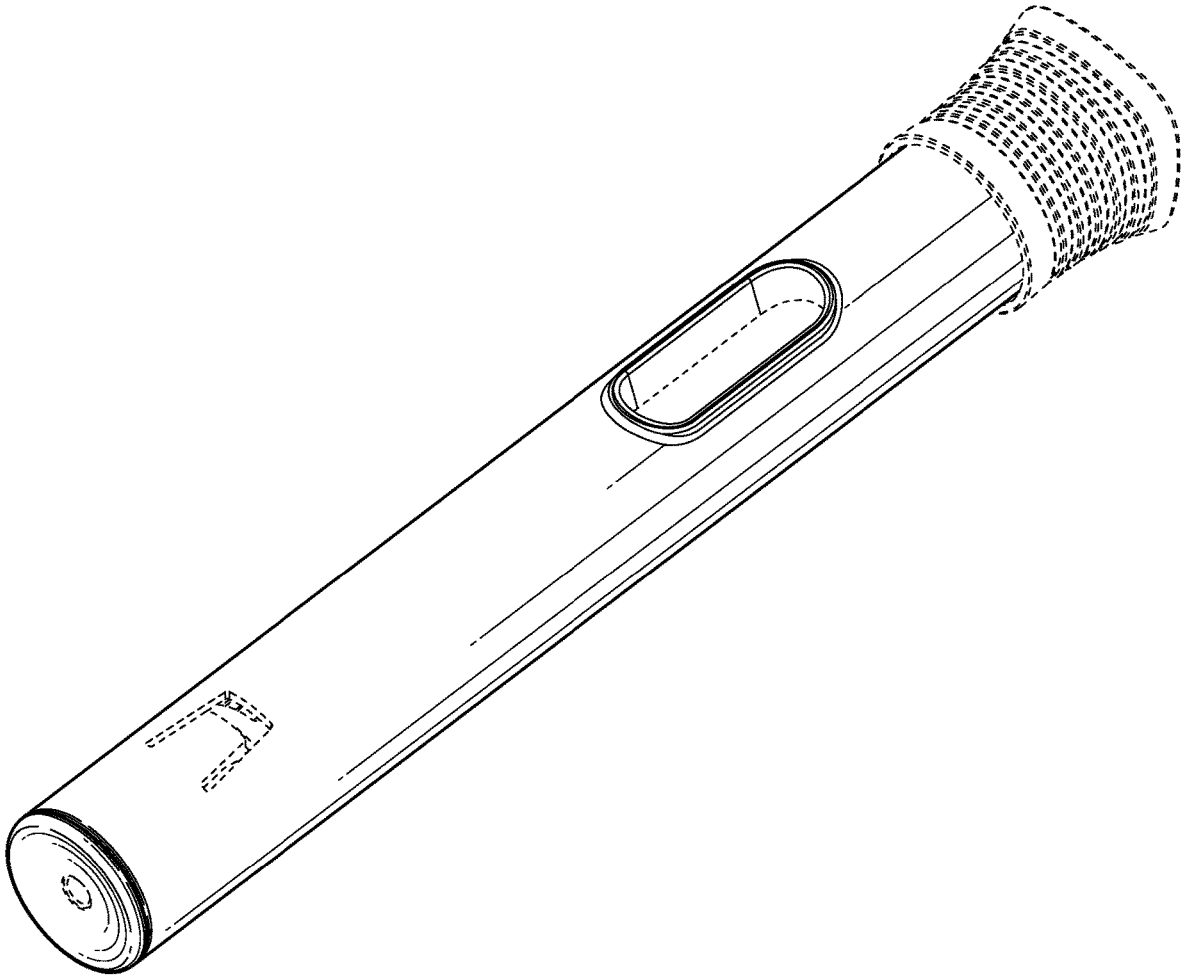
FIG. 2
(AMENDED)

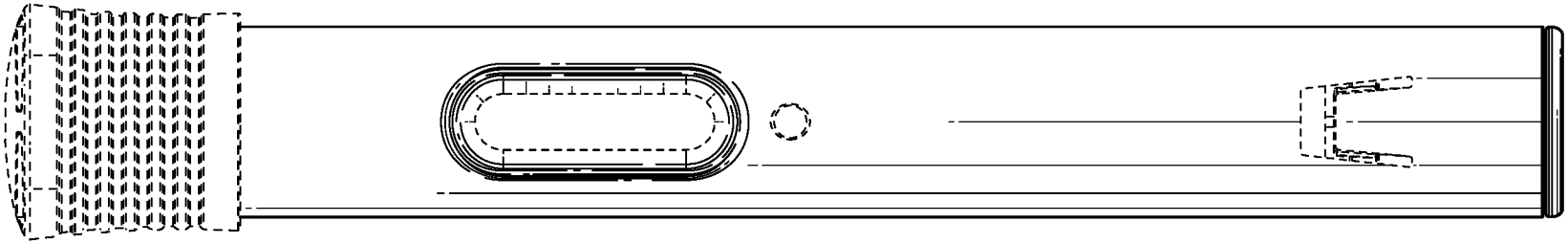
FIG. 3
(AMENDED)
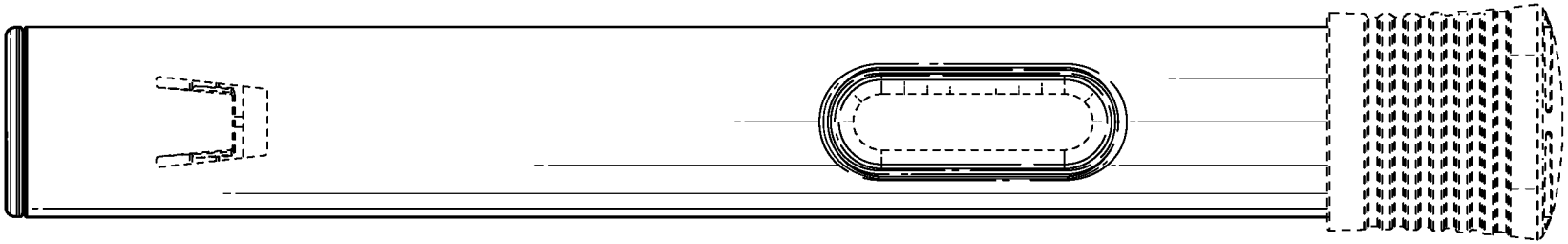
FIG. 4
(AMENDED)

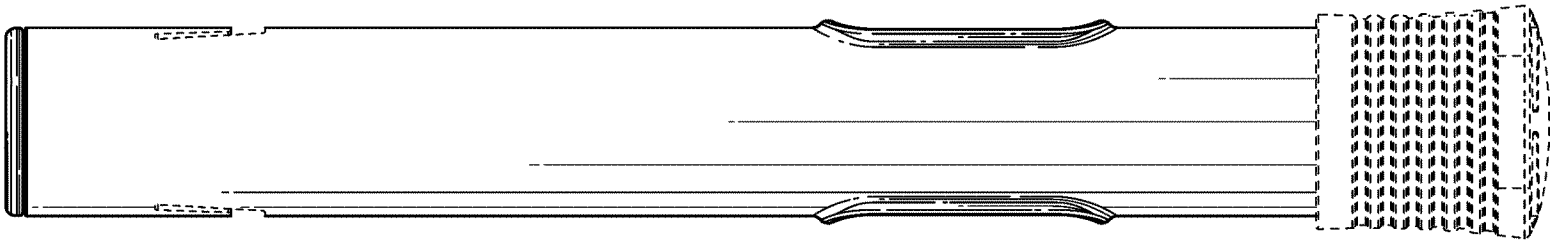
FIG. 5
(AMENDED)
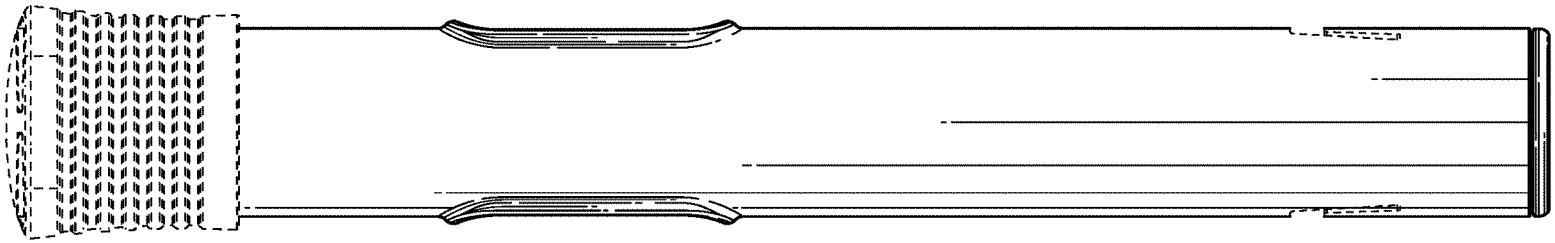
FIG. 6
(AMENDED)

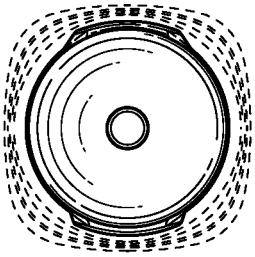
FIG. 7
(AMENDED)
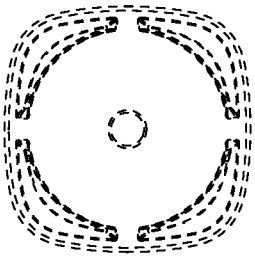
FIG. 8
(AMENDED)